United States Patent
Crump et al.

(10) Patent No.: US 7,327,850 B2
(45) Date of Patent: Feb. 5, 2008

(54) SUPPLYING ELECTRICAL POWER

(75) Inventors: Steve Crump, Wayland, MA (US); Daniel M. Gauger, Jr., Cambridge, MA (US); Robert Belanger, Franklin, MA (US)

(73) Assignee: Bose Corporation, Framingham, MA (US)

( * ) Notice: Subject to any disclaimer, the term of this patent is extended or adjusted under 35 U.S.C. 154(b) by 757 days.

(21) Appl. No.: 10/619,789

(22) Filed: Jul. 15, 2003

(65) Prior Publication Data

US 2005/0013447 A1    Jan. 20, 2005

(51) Int. Cl.
- *H04R 1/10* (2006.01)
- *H04R 1/00* (2006.01)
- *H04R 25/00* (2006.01)
- *A61F 11/06* (2006.01)
- *H03B 29/00* (2006.01)

(52) U.S. Cl. .................. 381/74; 381/71.6; 381/72; 381/71.1; 381/370; 381/323

(58) Field of Classification Search ............... 381/71.6, 381/72, 74, 370, 323
See application file for complete search history.

(56) References Cited

U.S. PATENT DOCUMENTS

| 3,873,904 | A  |   | 3/1975  | Kowalewski et al. |
| 5,353,347 | A  |   | 10/1994 | Irissou et al. |
| 6,069,959 | A  | * | 5/2000  | Jones ............ 381/71.6 |
| 6,118,878 | A  | * | 9/2000  | Jones ............ 381/72 |
| 6,704,428 | B1 |   | 3/2004  | Wurtz |
| 6,829,364 | B2 | * | 12/2004 | Andersen et al. ....... 381/323 |
| 2004/0258253 | A1 | * | 12/2004 | Wurtz ............ 381/71.6 |

FOREIGN PATENT DOCUMENTS

| JP | 10066334  | 3/1998 |
| JP | 200092830 | 3/2000 |
| WO | WO 0167805 | 9/2001 |

* cited by examiner

*Primary Examiner*—Vivian Chin
*Assistant Examiner*—Devona E Faulk
(74) *Attorney, Agent, or Firm*—Fish & Richardson P.C.

(57) ABSTRACT

A power supply includes a battery source supplying power and a voltage converter circuit. The voltage converter circuit converts the power to the input voltage supplied to other circuitry. The voltage converter circuit varies the input voltage in response to a load current drawn by the other circuitry from the power supply.

1 Claim, 7 Drawing Sheets

HIGH PSRR AMPLIFIER

SUPPLYING ELECTRICAL POWER

The present invention relates in general to supplying electrical power and more particularly concerns novel apparatus and techniques for supplying power to an active noise reduction headset.

BACKGROUND OF THE INVENTION

A typical prior art approach to active noise reduction (ANR) headsets uses a sensing microphone, which is located within close proximity to a small electro-acoustic transducer (sound source). The sensing microphone and the electro-acoustic transducer are both located within a circumaural earcup that clamps to the side of a user's head forming a closed cavity. Within the enclosed volume, the sensing microphone samples the sound present. The output of the microphone is fed to an on-board amplifier, inverted in polarity, and frequency compensated for stability to form a signal that is fed to the transducer (e.g., a speaker) that broadcasts a sound that reduces acoustic noise present within the earcup.

ANR headsets may also inject a desired signal elsewhere into the loop so that this desired signal is not reduced but rather faithfully reproduced. For example, communication signals and musical signals are inputted to the system in this manner, so the transducer can reproduce them to be heard by the user.

An important object of this invention is to provide an improved power supply.

Another object of the invention is to provide an improved power supply for an ANR headset.

BRIEF SUMMARY OF THE INVENTION

In one aspect, the invention is a power supply that includes a direct current (DC) voltage source that supplies power and a voltage converter circuit that converts the power to an input voltage supplied to an external circuit. The voltage converter circuit varies the input voltage in response to changes to a load current drawn by the external circuit from the power supply.

In another aspect, the invention is a power supply that includes a shutoff circuit that places an external circuit in a lower power consumption state when a load current, drawn from the external circuit by the power supply, falls below a threshold value for a predetermined amount of time.

In another aspect, the invention is an ANR headset system that includes a headset circuitry that receives an input voltage, and a power supply that provides the input voltage to the headset circuitry.

In still another aspect, the invention is ANR headset system that includes a shutoff circuit that places the headset circuitry in a lower power consumption state when a headset load current falls below a threshold value for a predetermined amount of time.

In a general aspect, by measuring a load current, a power supply varying the input voltage in response to a load current or having a shut-off circuit requires less circuitry to implement. In particular, this is advantageous to a power supply for ANR headsets, because less power is used thereby preserving battery life. In addition, less circuitry allows for ease in retrofitting power supplies to legacy ANR headsets.

Other features, objects and advantages will become apparent from the following detailed description when read in connection with the accompanying drawing in which:

DETAILED DESCRIPTION

Figure 1:
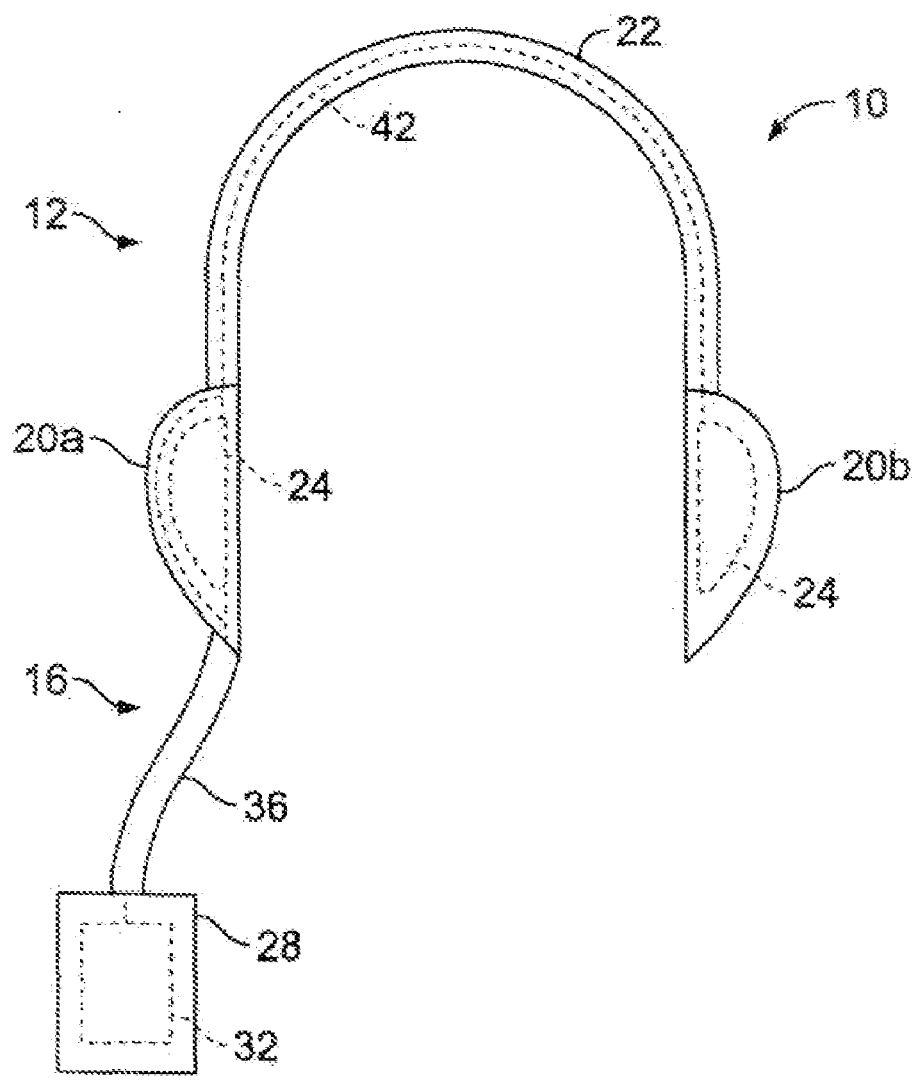
FIG. 1 is a diagram of an active noise reduction (ANR) system.

Referring to FIG. 1, an active noise reduction (ANR) system 10 includes a headset 12 and a power supply module 16. Headset 12 includes two earcups (e.g., left earcup 20a and right earcup 20b) and a headband 22 that connects to each of the earcups and holds them against a user's head. Each earcup 20a and 20b includes headset circuitry 24. Power supply module 16 includes a housing 28 that contains power supply circuitry 32. Power supply module 16 also includes a cable 36 that mechanically connects housing 28 to left earcup 20a (or, alternatively, to the right earcup 20b).

Cable 36 electrically connects power supply circuitry 32 to headset circuitry 24 of left earcup 20a and the cable electrically connects to headset circuitry 24 of right earcup 20b via electrical wires 42 within headband 22. In some embodiments, cable 36 is detachably connected to headset 12 allowing other power supplies to be used to power headset circuitry 24.

As will be shown below, power supply circuitry 32 provides a supply voltage $V_{CC}$ to each headset circuitry 24. The supply voltage $V_{CC}$ varies based on load current $I_H$ drawn by the headset circuitries 24 from the power supply circuitry 32.

Figure 2:
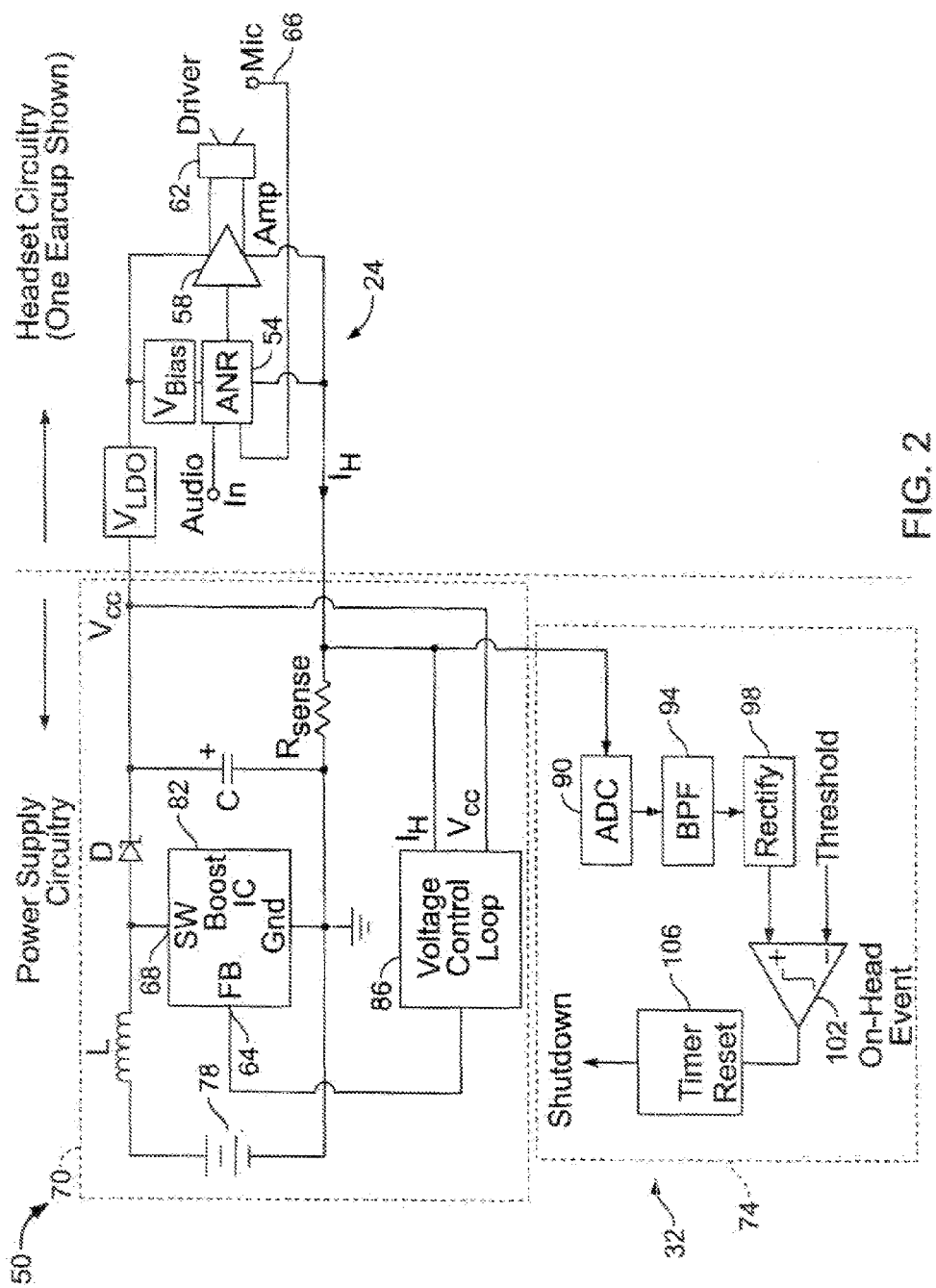
FIG. 2 is a block diagram of the ANR system.

Referring to FIG. 2, ANR system circuitry 50 includes power supply circuitry 32 supplying power to headset circuitry 24 in each earcup 20a and 20b (only one earcup of the two earcups is shown, the other is connected to $V_{CC}$ in parallel) Headset circuitry 24 includes a microphone 66 that detects sound signals in the earcup and transfers the sound signals to an ANR circuitry 54. ANR circuitry 54 supplies a noise reduction signal to reduce the undesired sound signals transmitted by microphone 66 and in turn transmits the noise reduction signal to a bridged-output amplifier 58. Amplifier 58 magnifies the noise reduction signal to driver 62 for broadcast within the earcup. Amplifier 58 is characterized by a high power supply rejection ratio (PSRR), which prevents production of an audible signal when the supply voltage $V_{CC}$ may vary rapidly. In some embodiments, amplifier 58 has a PSRR of at least 40 dB over the frequency range from DC to 10 kHz to ensure that rapid changes in $V_{CC}$ remain inaudible.

As the noise received by microphone 66 increases, headset circuitry 24 requires more power, most significantly by amplifier 58, and a greater load current $I_H$ is drawn in order to reduce the noise.

ANR circuitry 54 may also receive desired audio signals from external sources such as a stereo, a cassette player, a digital player, an intercom, a radio and the like, that is transmitted directly into each earcup 20*a* and 20*b* by way of an audio input to the ANR circuitry.

The supply voltage $V_{CC}$ received from power supply circuitry 32 passes through a voltage regulator $V_{LDO}$ prior to powering amplifier 58. Regulator $V_{LDO}$ is a low dropout regulator that regulates the supply voltage $V_{CC}$ down to a voltage level that is compatible with semiconductor components of headset circuitry 24, such as amplifier 58. When headset circuitry 24 is connected to the power supply 32, the supply voltage $V_{CC}$ does not exceed a predetermined regulated output voltage of $V_{LDO}$. Therefore, regulator $V_{LDO}$ does not operate in a regulation mode, and causes a small voltage drop across it. If headset circuitry 24 were alternatively connected to a different power supply module (i.e., not power supply module 16 but an alternate source of power), that is capable of supplying a voltage $V_{CC}$ that exceeds a maximum rated voltage of the components of headset circuitry 24, then regulator $V_{LDO}$ goes into a regulation mode by limiting the voltage supplied to these components to levels that will not damage them.

ANR circuitry 54 receives supply voltage $V_{CC}$ after the supply voltage passes through regulator $V_{LDO}$ and additionally regulator $V_{BIAS}$. Since the supply voltage $V_{CC}$ may be varied as a function of the load current drawn by headset circuitry 24, the voltage output from regulator $V_{LDO}$ may also vary. Regulator $V_{BIAS}$ adjusts a voltage received from regulator $V_{LDO}$ down to a fixed DC voltage to safely power ANR circuitry 54. By having a regulator $V_{BIAS}$, the need for high rejection of power supply variation by ANR circuitry is eliminated. For example, regulator $V_{BIAS}$ may regulate a voltage received from regulator $V_{LDO}$ that may vary from 2.8 up to 5.4 volts DC, down to a constant 2.5 volts DC. In other embodiments, regulator $V_{BIAS}$ is not included in headset circuitry 24.

Power supply circuitry 32 includes variable output power supply DC-DC conversion circuitry 70 and shut-off circuitry 74. Variable output power supply circuitry 70 includes direct current (DC) batteries 78 (e.g., 2 AA cells in series), a boost integrated circuit (IC) 82 and a voltage control loop (VCL) 86. In this embodiment, a boost topology is implemented, but other embodiments may implement other variable DC-DC conversion methods such as buck, boost/buck, or the like.

Boost IC 82 increases the voltage of DC batteries 78 to a supply voltage $V_{CC}$, in conjunction with inductor L, Schottky diode D, and capacitor C. Boost IC 82 uses the input received at a feedback (FB) pin 64 from VCL 86 to regulate the voltage $V_{CC}$. An example of a boost IC that may be implemented in this embodiment is a MAX1760 manufactured by Maxim Semiconductor of Sunnyvale Calif.

In a typical application, the supply voltage $V_{CC}$ would be connected to the FB pin 64 through a resistor divider; circuitry inside boost IC 82 then adjusts the operation of an internal switch (SW) pin 68 until the DC voltage at FB pin 64 equals an internal reference voltage. Varying the attenuation of the voltage divider changes the value of voltage present at the FB pin 64, which in turn varies the output voltage. The voltage at FB pin 64 therefore controls the output voltage of boost IC 82. Voltage control loop (VCL) 86 provides a signal to boost IC 82 through pin FB 64 that is a function of both the supply voltage $V_{CC}$ and the headset circuitry load current $I_H$ (measured by small valued current sensing resistor $R_{sense}$). VCL 86 varies $V_{CC}$ as a function of $I_H$ by varying the voltage applied to FB pin 64 of boost IC 82.

Figure 3:
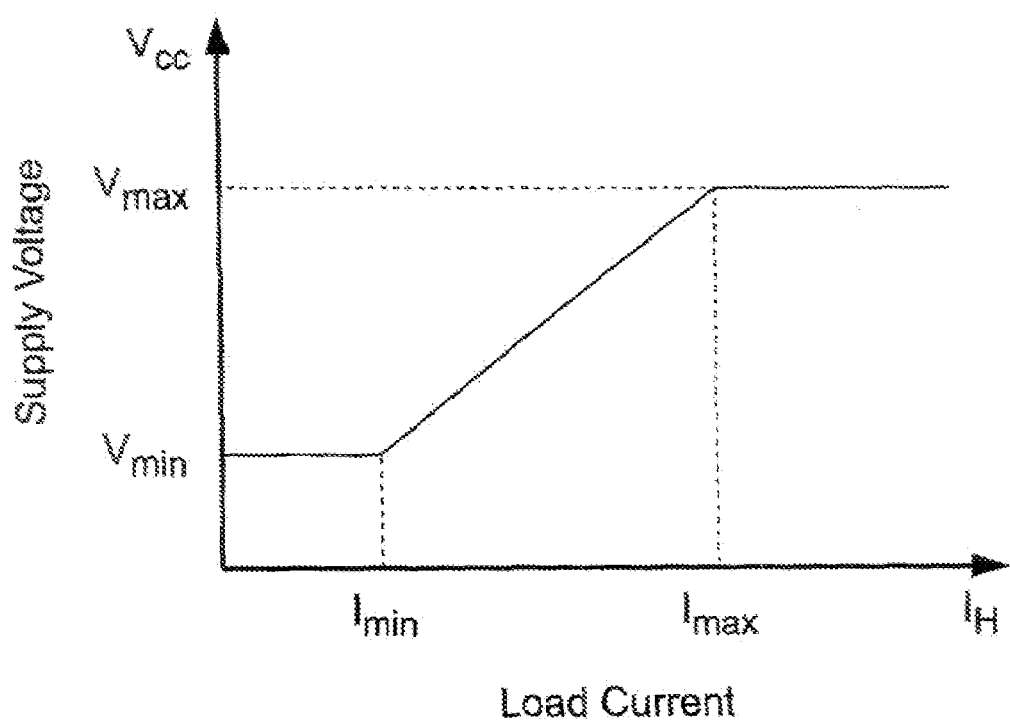
FIG. 3 is a graph of a supply voltage ($V_{CC}$) input to a headset circuitry versus a load current ($I_H$) of the headset circuitry.

FIG. 3 shows an exemplary effect of VCL 86. Below some minimum load current threshold $I_{min}$, the supply voltage $V_{CC}$ equals $V_{min}$, which is the minimum voltage headset circuitry 24 requires to operate in moderate noise conditions (e.g., 2.8 volts DC). Headset load current $I_H$ increases when the noise required to be reduced increases or the audio to be reproduced in the headset requires an increased output from amplifier 58. When the headset load current $I_H$ approaches $I_{min}$ the output voltage of amplifier 58 approaches a level at which clipping might occur.

Accordingly, to prevent clipping, when the load current $I_H$ exceeds $I_{min}$, VCL 86 causes the supply voltage $V_{CC}$ to increase, as some desired function (e.g., linear, exponential, discrete or the like) of the increasing headset load current $I_H$. The supply voltage $V_{CC}$ increases until the load current $I_H$ reaches a maximum current threshold $I_{max}$. Any increase in the load current $I_H$ beyond the maximum current $I_{max}$ results in a supply voltage of $V_{max}$. The value for the maximum voltage $V_{max}$ may be determined by the maximum voltage at which some component, such as an integrated circuit (not shown) or driver 62, can safely be operated without damage.

By varying the supply voltage $V_{CC}$ as a function of the load current $I_H$ and minimizing the supply voltage $V_{CC}$ provided to the headset circuitry 24 to what is required at any instant in time, battery life of batteries 78 may be extended. In other embodiments, the minimum current $I_{min}$ and the maximum current $I_{max}$ are adjusted to reduce power consumption while ensuring that clipping in amplifier 58 or modulation of the supply $V_{CC}$ do not result in audible artifacts.

Other embodiments implement other load current-dependent variations in supply voltage $V_{CC}$ such as switching of the supply voltage $V_{CC}$ between two or more discrete values in response to changes in the load current $I_H$, or memory could be added to VCL 86 such that supply voltage $V_{CC}$ remains at a higher value for a short time after the headset load current $I_H$ decreases. Still other embodiments could apply the invention to other converter circuits (e.g., buck or step-down) to minimize headset power consumption from other power sources.

Amplifier 58 has sufficient power supply rejection (PSR) so that large variations in power supply input result in very small output signals. In one embodiment, the PSR is at least 40 dB over the frequency range of DC to 10 kHz.

Figure 4A:
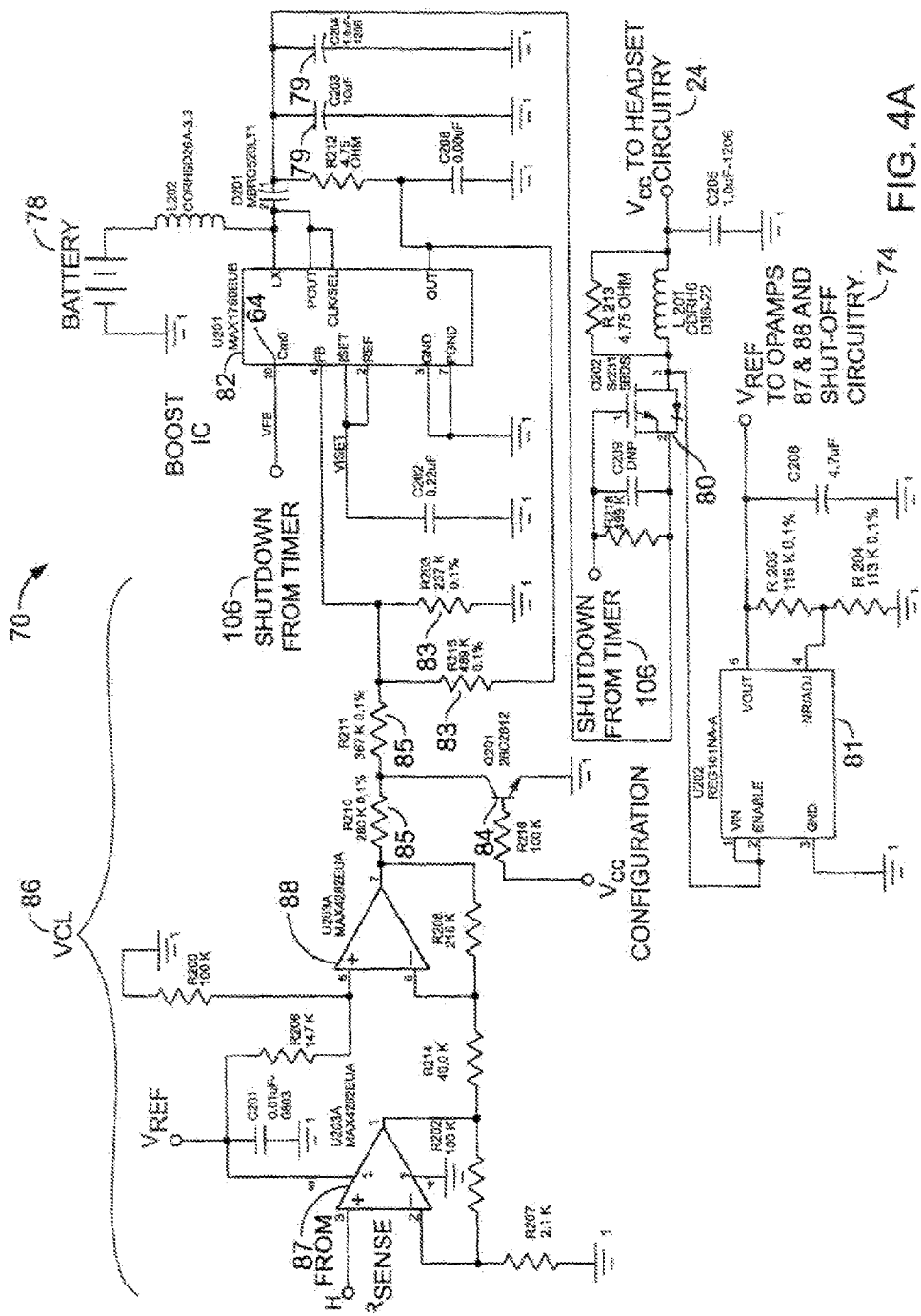
FIG. 4A is an electrical schematic of an example of a power supply circuitry.

Referring to FIG. 4A, boost IC 82 produces an output voltage on capacitors 79. Resistors 83 feeds back the output voltage on the capacitors to the FB pin 64 of boost IC 82 to allow its internal circuitry to regulate the output voltage. In the absence of the VCL circuitry 86, this voltage would be fixed and determined by the values of resistors 83.

VCL 86 includes two operational amplifiers (opamp) (e.g., opamp 87 and opamp 88) and associated passive components. Opamp 87 amplifies the voltage from resistor $R_{sense}$ (FIG. 2). Opamp 88 further amplifies the headset load current $I_H$, offsets it by a fixed voltage determined by reference voltage $V_{ref}$, and inverts it.

The output of opamp 88 is coupled to pin FB 64 through resistors 85. When opamp 88 is at its positive output limit (corresponding to $I_H=I_{min}$) this current signal combines with the voltage feedback through resistors 85 and 83 respectively to produce a signal at boost IC pin FB 64 that causes the boost IC output voltage to be $V_{min}$. As the headset load current $I_H$ increases, the output of opamp 88 decreases and boost IC increases its output voltage to maintain a constant value at FB pin 64. When $I_H=I_{max}$, opamp 88 reaches its negative output limit and the boost IC output is $V_{max}$. The output of boost IC 82 is connected to headset circuitry 24 through field effect transistor (FET) 80, which is "on" during normal operation. Regulator IC 81 regulates this output ($V_{CC}$) down to lower fixed voltage $V_{ref}$ to power opamp 87 and opamp 88 and other power supply circuitry.

In a typical ANR system, when a headset is worn, there are small periodic movements by the user, such as jaw and head movements that cause very low frequency acoustic signals to occur within the enclosed earcup. These movements are caused by small volume changes of the closed cavity, which result in pressure changes. The ANR system detects these changes and attempts to reduce these low frequency signals, which results in power being supplied to headset circuitry and low frequency variations in the load current drawn from the power supply. The presence or absence of these low frequency variations in load current are detected and used to indicate whether or not the headset is being worn. When it is determined that the headset is not being worn (by determining that the low frequency current variations have been below a predetermined threshold value for a predetermined period of time,) the operating state of the system is changed to a state that consumes minimal power (i.e., put into a "stand-by" mode of operation).

Referring back to FIG. 2, shut-off circuitry 74 includes an analog-to-digital converter (ADC) 90, a band-pass filter (BPF) 94, a rectifier 98, a comparator 102 and a timer 106. The measure of the headset load current $I_H$ passes through ADC 90 and then through BPF 94 and is rectified by rectifier 98. The resultant filtered current signal passes through to comparator 102, which compares the filtered current signal to a threshold. If the filtered current signal exceeds the threshold, a signal is sent to reset timer circuit 106. If the timer 106 is not reset by a predetermined time, a SHUTDOWN signal is sent to power circuit 32 to turn off the power supply.

In this embodiment, BPF 94 is a digital two-pole filter with a bandwidth from 1 Hz to 30 Hz and the predetermined time is one minute.

In other embodiments, circuitry 74 which includes ADC 90, BPF 94, comparator 102 and timer 106 may be implemented in a single microcontroller. In other embodiments, circuitry 74 may be implemented as discrete analog and/or digital functional circuits.

In other embodiments, BPF 94 may precede ADC 90 and be implemented in analog circuitry. In other embodiments, ADC 90 may be eliminated and all functions in shut-off circuitry 74 implemented using analog and discrete logic components. In still further embodiments, BPF 90 may be eliminated or changed to a low-pass filter if the threshold input to comparator 102 is changed appropriately.

Referring back to FIG. 4A, the SHUTDOWN signal from timer 106 connects to boost IC 82 to disable its operation and also to FET 80 to disconnect headset circuitry 24 from the power source. FET 80 also disconnects power from the input to regulator IC 81 and, in so doing, removes power from other power supply circuitry including opamp 87 and opamp 88, and shut-off circuitry 74. Additional circuitry (not shown) provides a small amount of power to shut-off circuitry 74 so that, when an "on" button is pushed, the shut-off circuitry will initiate power supply operation by changing the state of the SHUTDOWN signal, turning on boost IC 82 and power ($V_{CC}$) to headset circuitry 24.

VCL 86 includes a transistor 84 which, when turned "on" by signal $V_{CC}$ CONFIGURATION, disconnects the headset load current $I_H$ signal from boost IC 82 pin FB. Transistor 84, along with appropriately chosen values for resistors 85, cause the supply voltage $V_{CC}$ to be a fixed high value, and is no longer variable with load current. With this configuration, an improved power supply circuitry 32 having automatic shutoff provided by circuitry 74 may be used with older headsets that do not include the improvements in headset circuitry 24 such as high PSRR amplifier 58, which are advantageous for use with a variable voltage supply.

Voltage control loop 86 causes $V_{CC}$ to vary in direct proportion to the headset load current $I_H$ when $I_{min} < I_H < I_{max}$. This minimizes the voltage supplied to the headset circuitry 24 at each instant of time and thereby minimizes the power consumption of the headset.

Figure 4B:
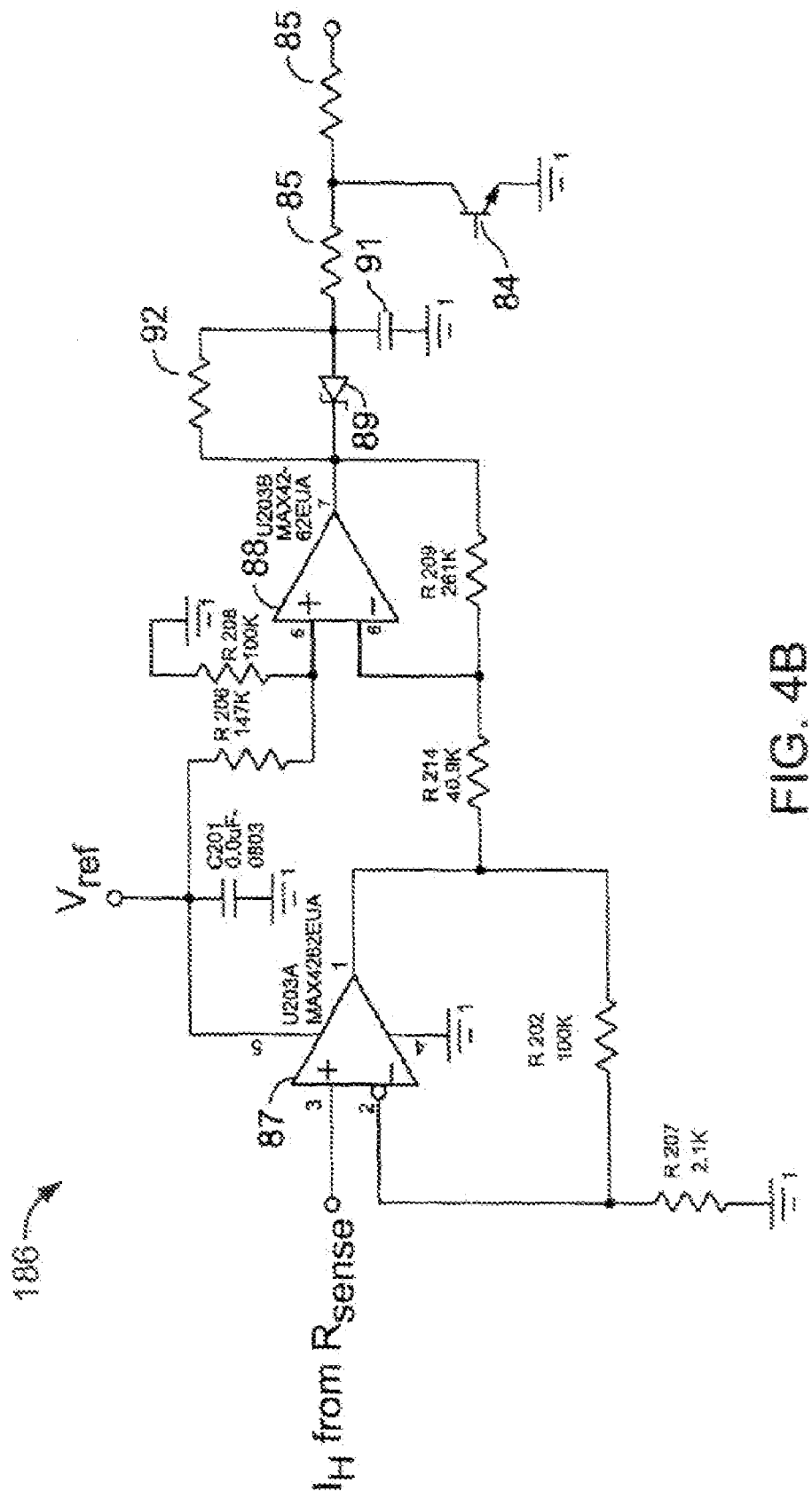
FIG. 4B is an electrical schematic of an example of a voltage control loop circuitry with an additional diode and capacitor.

Referring to FIG. 4B, in other embodiments, a VCL 186 further including a diode 89, capacitor 91, and a resistor 92 could be used so that the supply voltage $V_{CC}$ rises rapidly in response to increases in the headset load current $I_H$ but decreases slowly after headset load current $I_H$ decreases. In other embodiments, the VCL may be configured to vary between two or more discrete values rather than continuously as the headset load current $I_H$ changes.

Figure 5:
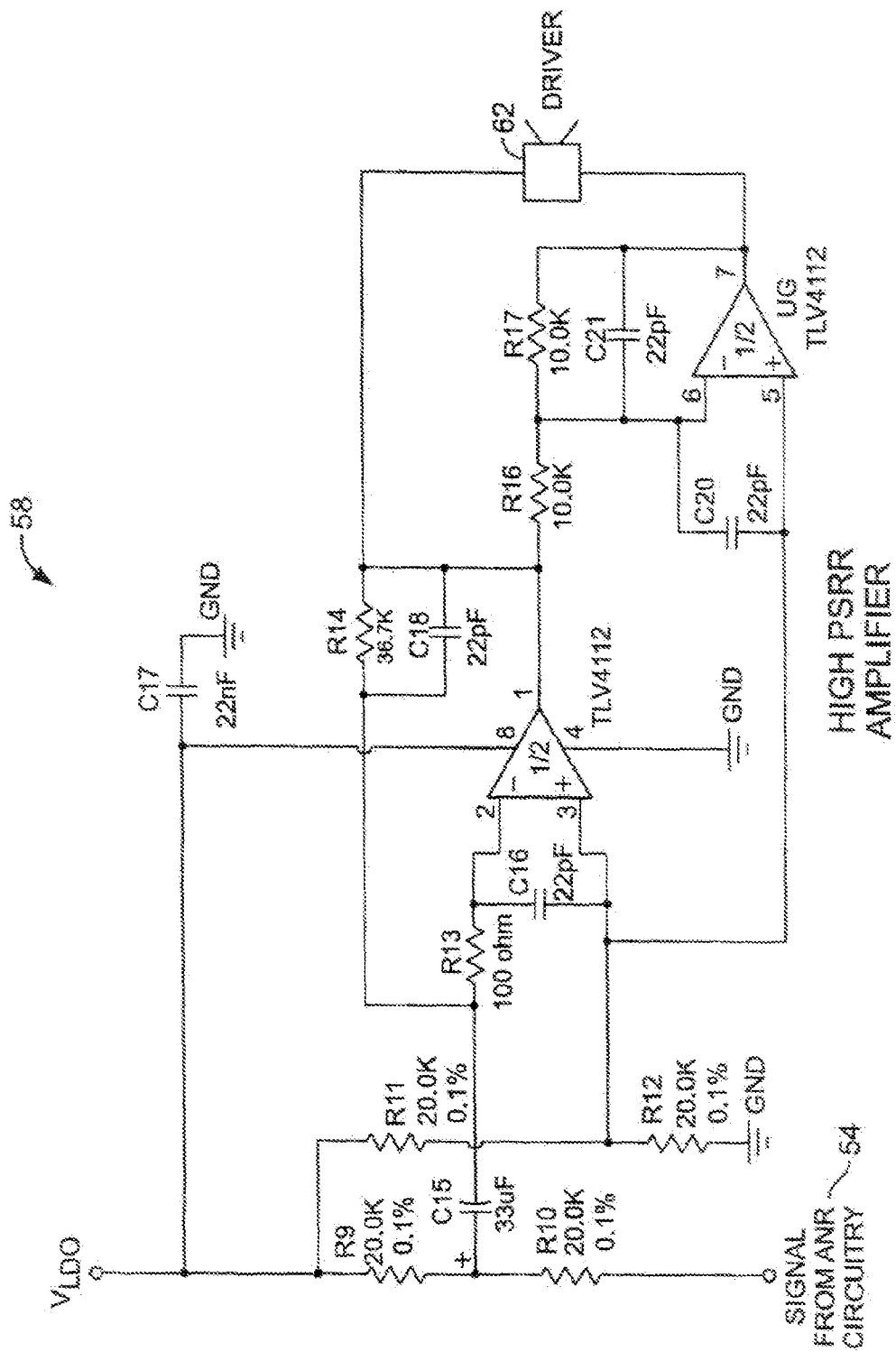
FIG. 5 is an electrical schematic of an example of an amplifier in the headset circuitry.

An example of an implementation of a high PSRR amplifier 58 is shown in FIG. 5. Amplifier 58 produces a bridged-mode output that is connected to driver 62. If the input signal from ANR circuitry 54 is zero, then each output of the bridged-mode amplifier is a voltage equal to $V_{LDO}/2$ and no voltage appears across driver 62. If the signal from ANR circuitry 54 is non-zero then that signal, magnified by an amount determined by the values of the various resistors in the circuit, is produced across driver 62. If this magnified signal across driver 62 results in a headset load current $I_H$ on the power supply circuit greater than $I_{min}$, causing $V_{CC}$ and, accordingly, $V_{LDO}$ to increase, then the voltages at each output terminal of amplifier 58 increase to a new value of $V_{LDO}/2$, plus or minus the desired output signal. The change in $V_{LDO}$ produces no output signal across the driver, to the extent that the values of the resistors are appropriately matched.

Figure 6:
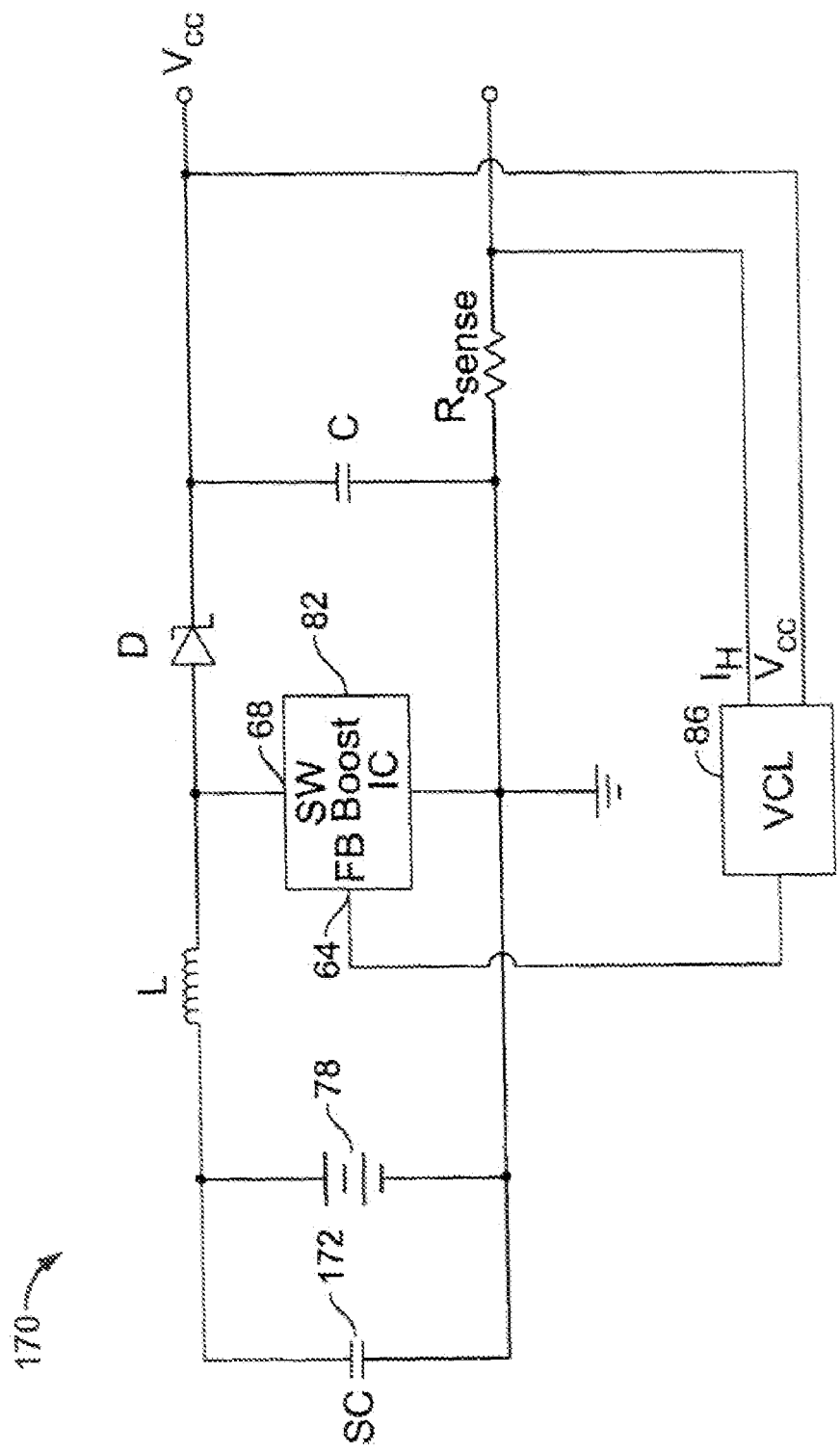
FIG. 6 is a block diagram of an example of a voltage converter circuit with a super-capacitor.

Referring to FIG. 6, in other embodiments power circuit 170 includes an energy storage device 172 which may be a capacitor or a super-capacitor (SC), connected in parallel to batteries 78. Adding energy storage device 172 further extends the life of batteries 78. The internal impedance of battery 78 causes its output voltage to decrease when high currents are drawn by the boost circuit. As the battery voltage decreases, the boost circuit must amplify the voltage by a larger amount to achieve a given output voltage $V_{CC}$; load currents drawn by the headset circuitry are in turn amplified by approximately the increased amount and drawn from the battery. For short pulses in load current, the voltage from the battery, particularly if nearly fully discharged, can decrease to the point that the boost circuit can no longer operate. By connecting energy storage device 172 such as a super capacitor in parallel with battery 78, the effective impedance of the power source is reduced. Variation in the power source voltage, caused by changing load currents reflected to the input, is therefore also reduced, allowing the battery to be operated deeper into its discharge profile. By using a parallel energy storage device, the battery need only be chosen to supply the average power required by the headset, and not the peak power.

There has been described novel apparatus and techniques for supplying power. It is evident that those skilled in the art may now make numerous modifications and uses of and departures from specific apparatus and techniques herein disclosed without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. An active noise reduction (ANR) headset system comprising:
   a headset circuitry receiving an input voltage; and
   a power supply providing the input voltage to the headset circuitry, the power supply comprising:
   a direct current (DC) voltage source supplying power; and
   a voltage converter circuit converting the power to the input voltage supplied to the headset circuitry, the voltage converter circuit varying the input voltage in response to changes to a headset load current drawn by the headset circuitry from the power supply,
   a shutoff circuit placing the headset circuitry in a lower power consumption state when the headset load current falls below a threshold value for a predetermined amount of time, wherein the headset circuitry comprises:
   an ANR circuit receiving a signal from a microphone positioned in an earcup and including a feedback loop to actively reduce the signal;
   a first voltage regulator limiting a voltage supplied to the ANR circuit and to an amplifier to a first predetermined voltage; and
   a second voltage regulator limiting the input voltage of the headset circuitry to a second predetermined voltage.

* * * * *